(12) United States Patent
Markosyan

(10) Patent No.: US 9,055,761 B2
(45) Date of Patent: *Jun. 16, 2015

(54) **GLUCOSYL *STEVIA* COMPOSITION**

(71) Applicant: PureCircle USA Inc., Oak Brook, IL (US)

(72) Inventor: Avetik Markosyan, Yerevan (AM)

(73) Assignee: PureCircle USA Inc., Oak Brook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/519,403

(22) Filed: Oct. 21, 2014

(65) Prior Publication Data

US 2015/0037462 A1 Feb. 5, 2015

Related U.S. Application Data

(63) Continuation of application No. 13/984,884, filed as application No. PCT/US2011/035173 on May 4, 2011, now Pat. No. 8,911,971, which is a continuation-in-part of application No. 13/029,263, filed on Feb. 17, 2011, now Pat. No. 8,257,948, which is a continuation-in-part of application No. 13/074,179, filed on Mar. 29, 2011, now Pat. No. 8,318,459.

(51) Int. Cl.
| | |
|---|---|
| *C12P 19/56* | (2006.01) |
| *C12P 7/02* | (2006.01) |
| *C12P 7/62* | (2006.01) |
| *A23L 1/236* | (2006.01) |
| *A61K 36/28* | (2006.01) |

(Continued)

(52) U.S. Cl.
CPC ............ *A23L 1/2365* (2013.01); *C12P 7/62* (2013.01); *C12P 7/02* (2013.01); *A61K 36/28* (2013.01); *C12P 19/14* (2013.01); *C12P 19/18* (2013.01); *A21D 13/08* (2013.01); *A23L 1/2363* (2013.01); *A23L 1/2366* (2013.01); *C07H 15/24* (2013.01); *C12P 19/56* (2013.01); *A23C 9/1307* (2013.01); *A23L 2/02* (2013.01); *A23L 2/60* (2013.01); *A23V 2002/00* (2013.01)

(58) Field of Classification Search
None
See application file for complete search history.

(56) References Cited

U.S. PATENT DOCUMENTS

| 3,723,410 A | 3/1973 | Persinos |
|---|---|---|
| 4,082,858 A | 4/1978 | Morita et al. |

(Continued)

FOREIGN PATENT DOCUMENTS

| BR | P10701736 | 7/2008 |
|---|---|---|
| CN | 1049666 | 3/1991 |

(Continued)

OTHER PUBLICATIONS

A-Glucosyltransferase Treated *Stevia*, Japan's Specifications and Standards for Food Additives, VIII edition, 2009, p. 257.

(Continued)

*Primary Examiner* — Blaine Lankford
*Assistant Examiner* — Charles Zoltan Constantine
(74) *Attorney, Agent, or Firm* — Briggs and Morgan, P.A.; Aleya R. Champlin; Audrey J. Babcock

(57) ABSTRACT

Glucosyl *stevia* compositions are prepared from steviol glycosides of *Stevia rebaudiana* Bertoni. The glucosylation was performed by cyclodextrin glucanotransferase using starch as the source of glucose residues. The short-chain glucosyl *stevia* compositions were purified to >95% content of total steviol glycosides. The compositions can be used as sweetness enhancers, flavor enhancers and sweeteners in foods, beverages, cosmetics and pharmaceuticals.

23 Claims, 2 Drawing Sheets

(51) Int. Cl.
  *C12P 19/14* (2006.01)
  *C12P 19/18* (2006.01)
  *A21D 13/08* (2006.01)
  *C07H 15/24* (2006.01)
  *A23C 9/13* (2006.01)
  *A23L 2/02* (2006.01)
  *A23L 2/60* (2006.01)

(56) References Cited

U.S. PATENT DOCUMENTS

| | | | |
|---|---|---|---|
| 4,171,430 A | 10/1979 | Matsushita et al. |
| 4,219,571 A | 8/1980 | Miyake |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | le Grand et al. |
| 4,892,938 A | 1/1990 | Giovanetto |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,011 B2 | 11/2010 | Modi |
| 7,862,845 B2 | 1/2011 | Magomet et al. |
| 8,257,948 B1 | 9/2012 | Markosyan |
| 2002/1322320 | 9/2002 | Wang et al. |
| 2003/0161876 A1 | 8/2003 | Hansson et al. |
| 2003/0236399 A1 | 12/2003 | Zheng et al. |
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0112155 A1 | 5/2010 | Abelyan et al. |
| 2010/0120710 A1 | 5/2010 | Watanabe et al. |
| 2010/0137569 A1 | 6/2010 | Prakash et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Liu |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 57002656 | 1/1981 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |

(56) References Cited

FOREIGN PATENT DOCUMENTS

| | | |
|---|---|---|
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009108680 | 9/2009 |
| WO | WO2010057024 | 5/2010 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |

OTHER PUBLICATIONS

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from *Stevia* glycosides by a novel adsorbent with pyridyl group", Science in China, vol. 42, No. 3 1999, 277-282.
Chen, et al., "Selectivity of polymer adsorbent in adsorptive separations of *Stevia* diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the *Stevia* plant", Chemistry in Britain, Oct. 1986, 915-916, 918.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
"Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of *Bacillus macerans*", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, mailed Aug. 5, 2011.
International Search Report and Written Opinion of PCT/US2011/047498, mailed Dec. 22, 2011.
International Search Report and Written Opinion of PCT/US2011/047499, mailed Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from *Stevia rebaudiana (Bertoni)*", Phytochem. Anal. vol. 20 2009, 240-245.
Kennelly, "Sweet and non-sweet constituents of Stevia rebaudiana", *Stevia*: The genus *Stevia*, Taylor & Francis, 2002, 68-85.
Kinghorn, "Overview", *Stevia*: The genus *Stevia*, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from *Stevia rebaudiana*", Phytochemistry, vol. 16 1977, 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from *Stevia rebaudiana*", Phytochemistry, vol. 15 1976, 981-983.
Kovylyaeva, et al., "Glycosides from *Stevia rebaudiana*", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous *Stevia*-extract in fixed-bed column with zeolites", Brazilian Journal of Chemical Engineering, vol. 21, No. 3 2004, 449-458.
Moraes, et al., "Clarification of *Stevia rebaudiana* (Bert.) Bertoni extract adsorption in modified zeolites", Acta Scientiarum, vol. 23, No. 6 2001, 1375-1380.
Ohta et al., "Characterization of Novel Steviol Glycosides from Leaves of *Stevia rebaudiana* Morita," J. Appl. Glycosi., vol. 57, 199-209, 2010.
Ohtani et al. "Chapter 7. Methods to improve the taste of the sweet principles of *Stevia rebaudiana*." The Genus *Stevia*, edited by A. Douglas Kinghorn, CRC Press 2001, Taylor and Francis, London and New York, pp. 138-159.
Phillips, K. C., "*Stevia*: steps in developing a new sweetener", In T.H. Grenby, Editor, Developments in Sweeteners-3, Elsevier 1987, 1-43.

(56) References Cited

OTHER PUBLICATIONS

Pol, et al., "Comparison of two different solvents employed for pressurised fluid extraction of stevioside from *Stevia rebaudiana*: methanol versus water", Anal Bioanal Chem vol. 388 2007, 1847-1857.

Prakash et al., "Development of rebiana, a natural, non-caloric sweetener," Jul. 1, 2008, Food and Chemical Toxology, vol. 46, Is. 7, Sup. 1, p. S75-S82.

Richman et al., "Fuctional genomics uncovers three glucosyltransferases involved in the synthesis of the major sweet glucosides of *Stevia rebaudiana*," The Plant Journal, vol. 41 (2005) 56-67.

Sakamoto et al., "Application of 13C NMR Spectroscopy to Chemistry of Natural Glycosides: Rebaudioside-C, a New Sweet Diterpene Glycoside of *Stevia rebaudiana*", Chem. Pharm. Bull., vol. 25, 1977, 844-846.

Shi, et al., "Synthesis of bifunctional polymeric adsorbent and its application in purification of *Stevia* glycosides", Reactive & Functional Polymers, vol. 50 2002, 107-116.

Shibata et al., "Glucosylation of Steviol and Steviol-Glucosides in Extracts from *Stevia rebaudiana* Bertoni," Plant Physiol. vol. 95, (1991) 152-156.

Starratt, et al., "Rebaudioside F, a diterpene glycoside from *Stevia rebaudiana*", Phytochemistry, vol. 59 2002, 367-370.

Sweet Green Fields, LLC, "Notice to the U.S. Food and Drug Administration (FDA) that the use of Rebiana (Rebaudiosid A) derived from *Stevia rebaudiana*, as a Food Ingredient is Generally Recognized as Safe (GRAS)," Jan. 15, 2009, http:/www.accessdata.fda.gov/scripts/fcn/gras_notices/grn000282.pdf (obtained from the WEB on May 8, 2012) entire document esp. p. 22, Table 1.

Tanaka, O., "Improvement of taste of natural sweeteners", Pure & Appl. Chem., vol. 69, No. 4 1997, 675-683.

Teo, et al., "Validation of green-solvent extraction combined with chromatographic chemical fingerprint to evaluate quality of *Stevia rebaudiana* Bertoni", J. Sep. Sci, vol. 32 2009, 613-622.

United Nations' Food and Agriculture Organization/Joint Expert Committee on Food Additives (2010) Steviol Glycosides, Compendium of Food Additive Specifications, FAO JECFA Monographs 10, 17-21.

van der Maarel et al., "Properties and applications of starch-converting enzymes of the a-amylase family," Journal of Biotechnology, vol. 94 (2002) 137-155.

Vasquez, Stimulation of the Gerbil's Gustatory Receptors by Some Potently Sweet Terpenoids, J. Agric. Food Chem., vol. 41, 1305-1310, 1993.

Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.

Yoda, et al., "Supercritical fluid extraction from *Stevia rebaudiana* Bertoni using CO2 and CO2+ water: extraction kinetics and identification of extracted components", Journal of Food Engineering, vol. 57 2003, 125-134.

Zell, et al., "Investigation of Polymorphism in Aspartame and Neotame Using Solid-State NMR Spectroscopy", Tetrahedron, vol. 56, 2000, 6603-6616.

Zhang, et al., "Membrane-based separation scheme for processing sweetener from *Stevia* leaves", Food Research International, vol. 33 2000, 617-620.

GLUCOSYL *STEVIA* COMPOSITION

CROSS-REFERENCE TO RELATED APPLICATIONS

The present invention claims the benefit of priority from and is: a Continuation application of U.S. application Ser. No. 13/984,884, filed Aug. 29, 2013, which is a 371 application of International Application No. PCT/US2011/035173, filed May 4, 2011, now expired; a Continuation-in-Part of U.S. Application No. 13/029,263, filed Feb. 17, 2011, now U.S. Pat. No. 8,257,948, issued Sep. 4, 2012; and a Continuation-in-Part of U.S. application Ser. No. 13/074,179, filed Mar. 29, 2011, now U.S. Pat. No. 8,318,459, issued Nov. 27, 2012. The contents of each of these applications are incorporated herein by reference in their entireties.

BACKGROUND OF THE INVENTION

1. Field of the Invention

The invention relates to a process for producing a highly purified food ingredient from the extract of the *Stevia rebaudiana* Bertoni plant and its use in various food products and beverages.

2. Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni, produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of *Stevia* are able to accumulate up to 10-20% (on dry weight basis) steviol glycosides. The major glycosides found in *Stevia* leaves are Rebaudioside A (2-10%), Stevioside (2-10%), and Rebaudioside C (1-2%). Other glycosides such as Rebaudioside B, D, E, and F, Steviolbioside and Rubusoside are found at much lower levels (approx. 0-0.2%).

Two major glycosides—Stevioside and Rebaudioside A, were extensively studied and characterized in terms of their suitability as commercial high intensity sweeteners. Stability studies in carbonated beverages confirmed their heat and pH stability (Chang S. S., Cook, J. M. (1983) Stability studies of stevioside and Rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, Rebaudioside A between 150 and 320 times, and Rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. *Pure Appl. Chem.* 69:675-683; Phillips K. C. (1989) *Stevia*: steps in developing a new sweetener. In: Grenby T. H. ed. Developments in sweeteners, vol. 3. Elsevier Applied Science, London. 1-43.)

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of *stevia* sweeteners are these undesirable taste attributes. It was shown that these flavor notes become more prominent as the concentration of steviol glycosides increases (Prakash I., DuBois G. E., Clos J. F., Wilkens K. L., Fosdick L. E. (2008) Development of rebiana, a natural, non-caloric sweetener. Food Chem. Toxicol., 46, S75-S82.)

Some of these undesirable properties can be reduced or eliminated by subjecting steviol glycosides to the reaction of intermolecular transglycosylation, when new carbohydrate residues are attached to initial molecule at C13 and C19 positions. Depending on the number of carbohydrate residues in these positions the quality and potency of the compounds taste will vary.

Pullulanase, isomaltase (Lobov S. V., Jasai R., Ohtani K., Tanaka O. Yamasaki K. (1991) Enzymatic production of sweet stevioside derivatives: transglycosylation by glucosidases. *Agric. Biol. Chem.* 55: 2959-2965), β-galactosidase (Kitahata S., Ishikawa S., Miyata T., Tanaka O. (1989) Production of rubusoside derivatives by transglycosylation of various β-galactosidase. *Agric. Biol. Chem.* 53: 2923-2928), and dextran saccharase (Yamamoto K., Yoshikawa K., Okada S. (1994) Effective production of glucosyl-stevioside by α-1, 6-transglucosylation of dextran dextranase. *Biosci. Biotech. Biochem.* 58: 1657-1661) have been used as transglycosylating enzymes, together with pullulan, maltose, lactose, and partially hydrolyzed starch, respectively, as donors of glycosidic residues.

The transglucosylation of steviol glycosides was also performed by action of cyclodextrin glucanotransferases (CG-Tase) produced by *Bacillus stearothermophilus* (U.S. Pat. Nos. 4,219,571, and 7,807,206) as a result α-1,4-glucosyl derivatives were formed with degree of polymerization up to 10.

It was shown (Tanaka O. (1987) Improvement of taste of natural sweetners. *Pure Appl. Chem.* 69:675-683) that the taste profile and sweetness power of glucosyl derivatives are largely dependent on number of additional α-1,4-glucosyl derivatives, i.e. the degree of polymerization of the α-1,4-glucosyl chain. However, in most of transgucosylated *stevia* products the degree of polymerization is usually below nine. As with any reaction, the transglucosylation reaction is inhibited by its products, and further increase of α-1,4-glucosyl residues is inhibited by reaction products, particularly short-chain maltooligosaccharides.

Therefore it is necessary to develop simple process of preparation of high purity glucosyl *stevia* products with greater α-1,4-glucosyl chain length and better taste profile.

SUMMARY OF THE INVENTION

The present invention is aimed to overcome the disadvantages of existing *Stevia* sweeteners. The invention describes a process for producing a high purity food ingredient from the extract of the *Stevia rebaudiana* Bertoni plant and use thereof in various food products and beverages as a sweetness and flavor modifier.

The invention, in part, pertains to an ingredient comprising glucosylated derivatives of steviol glycosides of *Stevia rebaudiana* Bertoni plant. The steviol glycodsides are selected from the group consisting of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof.

The invention, in part, pertains to a process for producing an ingredient containing glucosylated forms of stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant. The process can be an enzymatic transglucosylating process using CGTases produced by cultures of *Bacillus stearothermophilus*. The process may include the steps of decolorizing, desalting and removing maltooligosaccharides. The decolorizing can be performed using activated carbon. The desalting can be performed by passing through ion exchange resins and/or membrane filters. Removing the maltooligosaccharides can be performed by passing through macroporuos polymeric resin.

In the invention, *Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides amounting to total steviol glycosides' content of at least 95%, was used as a starting material. Alternatively *stevia* extracts with different ratio of steviol glycosides as well as highly purified steviol glycosides such as Rebaudioside A, stevioside, Rebaudioside D, rubusoside etc, may be used as starting materials.

The starting material was subjected to enzymatic transglucosylation by action of cyclodextrin glycosyltransferase (CGTase) in the presence of starch as a glucose donor. As a result α-1,4-glucosyl derivatives were formed with a degree of polymerization up to 9. Then the maltooligosaccharides from obtained reaction mixture were removed by Amberlite XAD7 HP resin. The resulting mixture of α-1,4-glucosyl derivatives (with a degree of polymerization up to 9) was subjected to the second enzymatic transglucosylation by CGTase in the presence of starch as a glucose donor. As a result of the second glucosylation, α-1,4-glucosyl derivatives with a degree of polymerization up to 20 were formed. The maltooligosaccharides obtained during second glucosylation were removed by Amberlite XAD7 HP resin. Then the obtained mixture of α-1,4-glucosyl derivatives (with degree of polymerization up to 20) was decolorized, deionized, concentrated and spray dried.

The obtained products were applied in various foods and beverages as sweeteners, sweetener enhancers and flavor modifiers, including ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Figure 1:
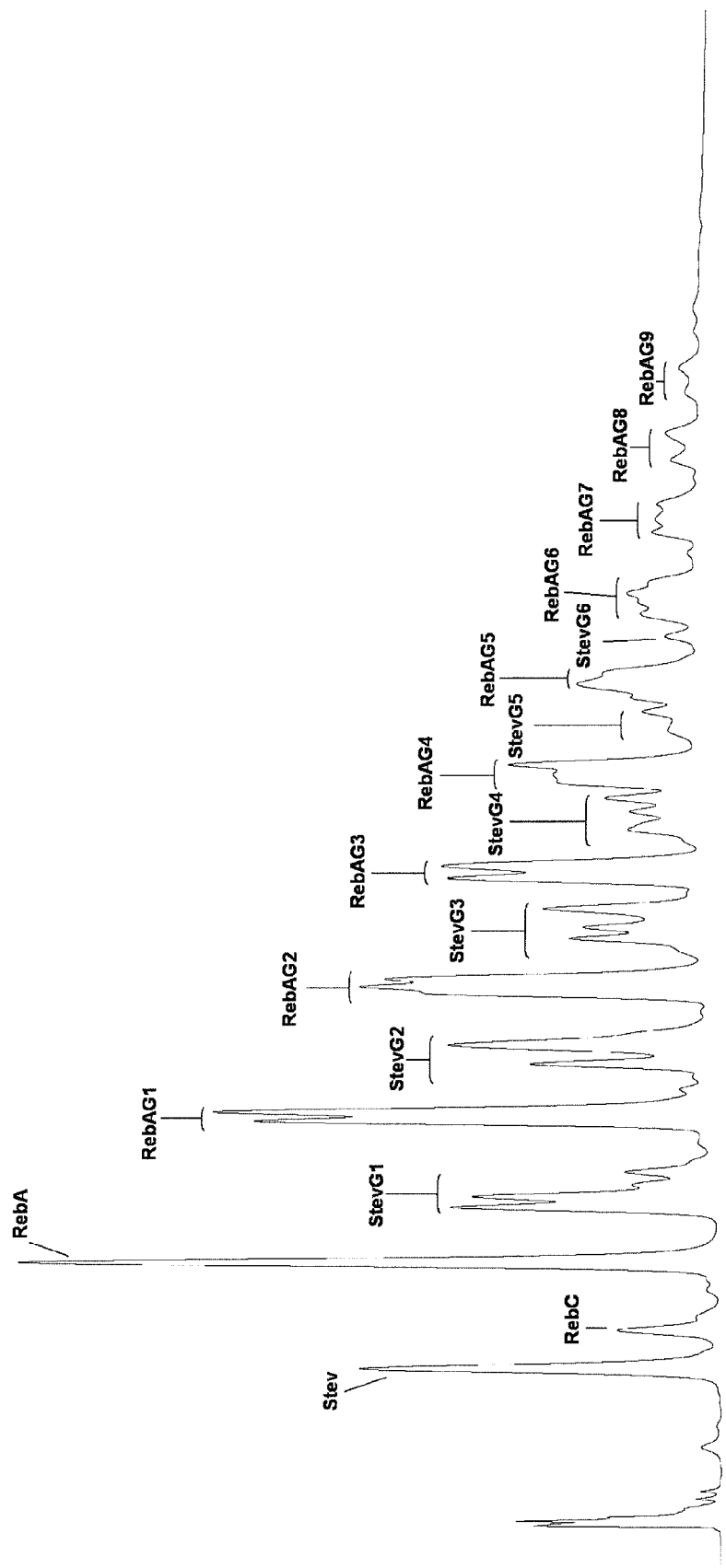
FIG. 1 shows a high-performance liquid chromatogram of transglucosylated *Stevia* extract containing α-1,4-glucosyl-derivatives with up to nine α-1,4-glucosyl residues.
Figure 2:
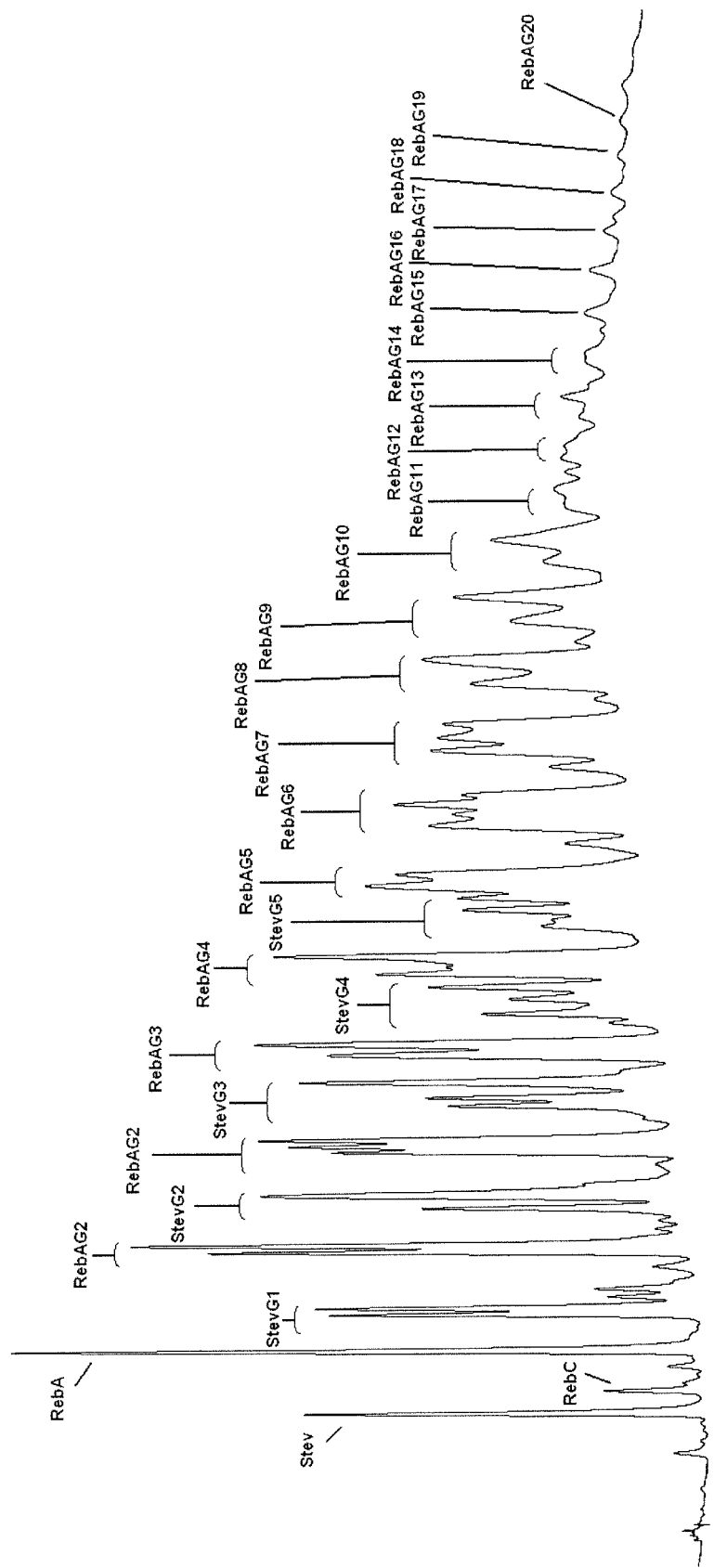
FIG. 2 shows a high-performance liquid chromatogram of transglucosylated *Stevia* extract containing α-1,4-glucosyl-derivatives with up to twenty α-1,4-glucosyl residues.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

*Stevia* extract commercialized by PureCircle (JiangXi) Co., Ltd. (China), containing stevioside (28-30%), Rebaudioside A (50-55%), Rebaudioside C (9-12%), Rebaudioside F (1-3%) and other glycosides (hereinafter collectively, "steviol glycosides") amounting to total steviol glycosides content of at least 95%, was used as a starting material. Alternatively *stevia* extracts with different ratio of steviol glycosides as well as highly purified steviol glycosides such as Rebaudioside A, stevioside, Rebaudioside D, rubusoside etc, may be used as starting materials.

The HPLC analysis of the raw materials and products was performed on Agilent Technologies 1200 Series (USA) liquid chromarograph, equipped with Zorbax-NH$_2$ (4.6×250 mm) column. The mobile phase was acetonitrile-water gradient from 80:20, v/v (0-2 min) to 50:50, v/v (2-70 min). A diode array detector set at 210 nm was used as the detector.

The transglucosylation was accomplished by cyclomaltodextrin glucanotransferases (CGTases; EC 2.4.1.19) produced by *Bacillus stearothermophilus* St-100 (PureCircle Sdn Bhd Collection of Industrial Microorganisms—Malaysia). However, any other CGTase or enzyme possessing intermolecular transglucosylation activity may be applied as well. The enzyme can be in a form of cell-free culture broth, concentrated liquid cell-free culture broth, spray dried or freeze dried cell-free culture broth, or high purity protein. Free and immobilized enzyme preparations can be used.

The activity of CGTase preparations was determined according to the procedure described in Hale W. S., Rawlins L. C. (1951) Amylase of *Bacillus macerans*. Cereal Chem. 28, 49-58.

Starches of different origin may be used as donors of glucosyl units such as, derived from wheat, corn, potato, tapioca, and sago.

Starch was subjected to partial hydrolysis (liquefaction) prior to the transglycosylation reaction. The dextrose equivalent of the partially hydrolyzed starch can be in the range of about 10-25, preferably about 12-16. Any enzyme capable of starch hydrolysis may be used for liquefaction, such as α-amylases, β-amylases etc. In one embodiment, CGTase and α-amylase mixtures as liquefying enzymes are preferred.

α-Amylase activity is expressed in Kilo Novo α-amylase Units (KNU). One KNU is the amount of α-amylase which, under standard conditions (pH 7.1; 37° C.), dextrinizes 5.26 g starch dry substance per hour.

The liquefaction mixture contains about 0.001-0.2 KNU, preferably about 0.05-0.1 KNU of α-amylase per one unit of CGTase.

The use of α-amylase in liquefaction allows achieving higher throughputs in further activated carbon filtration. When the CGTase is used as the only liquefying enzyme the filtration rate is approximately 10-15 L/hr per 1 m$^2$ of filter surface. In case of liquefaction enzyme mixture (comprising α-amylase and CGTase) the filtration rate is twice as fast—approximately 20-30 L/hr per 1 m$^2$ of filter surface.

The ratio of starch and CGTase in the liquefaction mixture is about 0.1-0.5 units per one gram of starch, preferably about 0.2-0.4 units per gram.

The concentration of starch in liquefaction mixture is about 15-40% (wt/wt), preferably about 20-30%.

The liquefaction is conducted at about 70-90° C. during about 0.5-5 hours, preferably about 1-2 hours.

After liquefaction, the reaction mixture is subjected to thermal inactivation of α-amylase at low pH conditions. The preferred pH range for inactivation is about pH 2.5 to pH 3.0 and preferred temperature is about 95-105° C. The duration of thermal inactivation is about 5-10 minutes.

After the inactivation, the pH of the reaction mixture is adjusted to about pH 5.5-6.5 and the steviol glycosides are added to the mixture and dissolved. The preferred ratio of steviol glycosides to starch (kg of steviol glycosides per 1 kg of starch) is about 0.5-1.5, preferably about 0.8-1.2.

A second portion of CGTase preparation is added and the first transglucosylation reaction is conducted at about 65° C. for about 24-48 hours. The amount of the second portion of CGTase is about 0.2-4 units of CGTase per gram of solids, preferably about 0.5-1.2 units per gram of solids.

Upon completion of transglucosylation the reaction was stopped by heating at about 95° C. for about 15 minutes to inactivate the enzyme. As a result a mixture of α-1,4-glucosyl derivatives with a degree of polymerization up to 9 was obtained. In order to remove the short chain maltoologisaccharides, which inhibit the further elongation of α-1,4-glucosydic chain, the reaction mixture was passed through a column packed with Amberlite XAD7 HP macroporous adsorbent resin. The steviol glycosides and their glucosylated derivatives were adsorbed on the resin and subsequently eluted by aqueous ethanol. The resulting aqueous ethanol eluate, containing glucosyl steviol glycosides, was evaporated, concentrated and spray dried to obtain transglucosylated Stevia extract containing glucosyl derivatives with up to nine α-1,4-glucosyl residues.

A second portion of starch was subjected to partial hydrolysis (liquefaction) as described above.

After the liquefaction the transglucosylated Stevia extract obtained during the first glucosylation (with up to nine α-1,4-glucosyl residues) was added. The preferred ratio of transglucosylated Stevia extract to starch (kg of transglucosylated Stevia extract per 1 kg of starch) is about 0.5-1.5, preferably about 0.8-1.2.

Another portion of the CGTase preparation was added and the second transglucosylation reaction was conducted at about 65° C. for about 24-48 hours. The amount of this portion of CGTase is about 0.2-4 units of CGTase per gram of solids, preferably about 0.5-1.2 units per gram of solids.

Upon completion of transglucosylation the reaction was stopped by heating at about 95° C. for about 15 minutes to inactivate the enzyme. As a result a mixture of α-1,4-glucosyl derivatives with a degree of polymerization up to 20 was obtained.

The maltooligosaccharides were removed from reaction mixture using Amberlite XAD7 HP resin as described above. The steviol glycosides and their glucosylated derivatives were adsorbed on the resin and subsequently eluted by aqueous ethanol. The resulted aqueous ethanol eluate, containing glucosyl steviol glycosides, was treated with activated carbon, to obtain decolorized reaction mixture. The amount of activated carbon was about 0.02-0.4 grams per gram of solids, preferably about 0.05-0.2 grams per gram of solids. The decolorized solution was further desalted by passing through ion exchange resins, such as Amberlite FPC23 (H⁺ type) and Amberlite FPA51 (OH⁻ type). Other appropriate decolorizing and desalting methods, such as membrane filtration, or other methods known in the art can be used.

The desalted reaction mixture was further concentrated by vacuum evaporator and dried by means of a spray dryer. Other appropriate concentrating and drying methods, such as membrane filtration, freeze drying, or other methods known to art can be used.

The resulting product was transglucosylated Stevia extract containing α-1,4-glucosyl-derivatives with up to twenty α-1,4-glucosyl residues (Sample 2).

The transglucosylated Stevia extract can optionally be further purified by removing unreacted steviol glycosides. The dried transglucosylated Stevia extract powder is suspended in aqueous alcohol. The powder to aqueous alcohol ratio (wt/vol) can range from 1:1 to 1:20, preferably 1:3 to 1:10. The aqueous alcohol contains 0-50% (vol), preferably 1-10% water. The suspension is agitated at 30-100° C., preferably 50-85° C. during 1-24 hours, preferably 2-15 hours. Then the suspended solids are separated by means of filtration. Any other technique known in the art suitable for separating suspended solids from liquid such as centrifugation, decanting, etc. can be used. The obtained solids are dried in rotary drum vacuum drier. Any other dryer known t in the art may be used as well. Alternatively the separated solids may be dissolved in water, evaporated from traces of alcohol and spray dried.

The alcohols employed in this optional step may be selected from the group consisting of alkanols, and are preferably selected from the group including methanol, ethanol, n-propanol, 2-propanol, 1 butanol, and 2-butanol.

The resulting product contains a low level of non-modified glycosides, even without the optional steviol glycoside removal step. As used herein, the expressions "low level non-modified glycosides" or "low level unreacted glycosides" shall refer to glycoside levels of less than about 20%, and preferably less than about 15%, on an anhydrous basis. In some embodiments, an unreacted glycoside level of less than about 12%, less than about 10% or even lower can be attained using this method. Performing the optional step of steviol glycoside removal results in even lower levels of unreacted steviol glycosides in the final product.

A small part of purified transglucosylated Stevia extract containing α-1,4-glucosyl-derivatives with up to nine α-1,4-glucosyl residues (obtained as described above) was separated and further subjected to decolorizing and desalting treatment (similar to Sample 2) to produce Sample 1.

The process used for preparing Sample 2 was repeated without removal of maltooligosaccharides from first transglucosylation mixture (containing α-1,4-glucosyl-derivatives with up to nine α-1,4-glucosyl residues). This process yielded Sample 3.

The analysis of each Sample's composition (Table 1) shows a similar composition for Samples 1 and 3, whereas Sample 2 had larger concentration of high glucosyl derivatives (containing up to 20 α-1,4-glucosyl residues).

TABLE 1

Composition of glucosyl steviol glycosides samples

| | Content, % | | |
|---|---|---|---|
| Compounds | Sample 1 | Sample 2 | Sample 3 |
| Stevioside | 3.1 | 1.6 | 2.9 |
| Rebaudioside C | 1.0 | 0.4 | 1.0 |
| Rebaudioside A | 6.1 | 2.8 | 5.8 |
| Monoglucosyl-stevioside (StevG1) | 7.4 | 3.7 | 7.5 |
| Monoglucosyl-Rebaudioside A (RebAG1) | 11.1 | 4.5 | 11.5 |
| Diglucosyl-stevioside (StevG2) | 8.4 | 4.8 | 8.8 |
| Diglucosyl-Rebaudioside A | 9.6 | 5.3 | 9.7 |

TABLE 1-continued

Composition of glucosyl steviol glycosides samples

| Compounds | Content, % | | |
|---|---|---|---|
| | Sample 1 | Sample 2 | Sample 3 |
| (RebAG2) Higher Glucosylated derivatives up to G9 | 48.4 | 57.5 | 49.3 |
| Higher Glucosylated derivatives from G9 to G20 | — | 15.6 | — |
| Total content of unreacted glycosides | 10.2 | 4.8 | 9.7 |
| Total content of glycosides | 95.8 | 96.2 | 96.5 |

The sensory assessment of samples was carried using aqueous solutions, with 20 panelists. Based on overall acceptance the most desirable and most undesirable samples were chosen. The results are shown in Table 2.

TABLE 2

Sensory assessment of samples in water system

| Judgment | Sample 1 | Sample 2 | Sample 3 |
|---|---|---|---|
| Most desirable | 1 | 18 | 1 |
| Sweetness power | 120 | 80 | 120 |
| Comments | Sweet, slightly bitter, astringent, slight lingering aftertaste, sweetness onset is slow | Sweet, light, soft, round, pleasant, similar to sucrose, no lingering aftertaste, sweetness onset is rapid | Sweet, slightly bitter, astringent, slight lingering aftertaste, sweetness onset is slow |

As apparent from the results in Table 2, the sweetness quality of the Sample 2 was rated as most superior.

The glucosyl *stevia* composition represented by Sample 2 shows comparable sweetness power (80 times sweeter compared to a 5% sucrose solution) with control Samples 1 and 3 (120 times); however its flavor profile was clearly superior to the control samples.

The composition can be used as sweetness enhancer, flavor enhancer and sweetener in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the composition can be used in drug or pharmaceutical preparations and cosmetics, including but not limited to toothpaste, mouthwash, cough syrup, chewable tablets, lozenges, vitamin preparations, and the like.

The composition can be used "as-is" or in combination with other sweeteners, flavors and food ingredients.

Non-limiting examples of sweeteners include steviol glycosides, stevioside, Rebaudioside A, Rebaudioside B, Rebaudioside C, Rebaudioside D, Rebaudioside E, Rebaudioside F, dulcoside A, steviolbioside, rubusoside, as well as other steviol glycosides found in *Stevia rebaudiana* Bertoni plant and mixtures thereof, *stevia* extract, Luo Han Guo extract, mogrosides, high-fructose corn syrup, corn syrup, invert sugar, fructooligosaccharides, inulin, inulooligosaccharides, coupling sugar, maltooligosaccharides, maltodextins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners, gelling agents.

The following examples illustrate various embodiments of the invention. It will be understood that the invention is not limited to the materials, proportions, conditions and procedures set forth in the examples, which are only illustrative.

Example 1

Preparation of CGTase

A strain of *Bacillus stearothermophilus* St-100 was inoculated in 2,000 liters of sterilized culture medium containing 1.0% starch, 0.25% corn extract, 0.5% $(NH_4)_2SO_4$, and 0.2% $CaCO_3$ (pH 7.0-7.5) at 56° C. for 24 hrs with continuous aeration (2,000 L/min) and agitation (150 rpm). The obtained culture broth was filtered using Kerasep 0.1 μm ceramic membrane (Novasep, France) to separate the cells. The cell-free permeate was further concentrated 2-fold on Persep 10 kDa ultrafilters (Orelis, France). The activity of the enzyme was determined according to Hale, Rawlins (1951). A crude enzyme preparation with activity of about 2 unit/mL was obtained.

Example 2

Preparation of Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of the reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g *stevia* extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to the liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was diluted with water to 5% solids content and passed through columns each packed with 4000 mL Amberlite XAD 7HP macroporous adsorbent resin. The columns were washed with 5 volumes of water and 2 volumes of 20% (v/v) ethanol. The adsorbed glycosides were eluted with 50% ethanol. The obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 151 grams of product was obtained (Sample 1).

Example 3

Preparation of Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g of transglucosylated *stevia* extract obtained according to EXAMPLE 2 was added to the liquefied starch and stirred until a homogeneous solution was obtained. 200 units of CGTase were added to the solution and the mixture was held at a temperature of 65° C. for 24 hours under continuous agitation. The obtained reaction mixture was heated at 95° C. for 15 minutes to inactivate the enzyme. 20 grams of activated carbon was added and the mixture was heated to 75° C. and held during 30 min. The mixture was filtered and the filtrate was diluted with water to 5% solids content and passed through columns each packed with 4000 mL Amberlite XAD 7HP macroporous adsorbent resin. The columns were washed with 5 volumes of water and 2 volumes of 20% (v/v) ethanol. The adsorbed glycosides were eluted with 50% ethanol. The obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 140 grams of product was obtained (Sample 2).

Example 4

Preparation of Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g *stevia* extract produced by PureCircle (JiangXi) Co., Ltd. (China), containing stevioside 29.2%, Rebaudioside A 54.3%, Rebaudioside C 9.0%, Rebaudioside F (1.7%) and other glycosides amounting to total steviol glycosides content of about 96.4% was added to liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzymes. 20 grams of activated carbon was added and the mixture was heated to 75° C. and held for 30 minutes. The mixture was filtered and the filtrate was passed through columns packed with Amberlite FPC23 (H$^+$) and Amberlite FPA51 (OH$^-$) ion exchange resins. 195 grams of product was obtained.

Example 5

Preparation of Glucosyl *Stevia* Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g of transglucosylated *stevia* extract obtained according to EXAMPLE 4 was added to liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzyme. 20 grams of activated carbon was added and the mixture was heated to 75° C. and held during 30 min. The mixture was filtered and the filtrate was diluted with water to 5% solids content and passed through columns each packed with 4000 mL Amberlite XAD 7HP macroporous adsorbent resin. The columns were washed with 5 volumes of water and 2 volumes of 20% (v/v) ethanol. The adsorbed glycosides were eluted with 50% ethanol. The obtained eluate was passed through columns packed with Amberlite FPC23 (H$^+$) and Amberlite FPA51 (OH$^-$) ion exchange resins. The ethanol was evaporated and the desalted and decolorized water solution was concentrated at 60° C. under vacuum, then dried into a powder form using laboratory spray dryer. 105 grams of product was obtained (Sample 3).

Example 6

Low-Calorie Orange Juice Drink

Orange concentrate (35%), citric acid (0.35%), ascorbic acid (0.05%), orange red color (0.01%), orange flavor (0.20%), Rebaudioside A (0.003%) and different glucosyl *stevia* compositions (0.03% for Samples 1 and 3 and 0.04% for Sample 2) were blended and dissolved completely in water (up to 100%) and pasteurized. Glucosyl *stevia* compositions were represented by Samples 1, 2, and 3, obtained according to EXAMPLES 2, 3 and 5, respectively.

The sensory evaluations of the samples are summarized in Table 3. The data show that the best results can be obtained by using the high purity glucosyl *stevia* composition (containing up to 20 α-1,4-glucosyl residues) (Sample 2). Particularly the drinks prepared with Sample 2 exhibited a rounded and complete flavor profile and mouthfeel.

TABLE 3

Evaluation of orange juice drink samples

| Sample | Flavor | Aftertaste | Mouthfeel |
|---|---|---|---|
| No. 1 | Sweet, licorice notes | Slight bitterness and aftertaste | Not acceptable |
| No. 2 | High quality sweetness, pleasant taste similar to sucrose, rounded and balanced flavor | Clean, no bitterness and no aftertaste | Full |
| No. 3 | Sweet, licorice notes | Slight bitterness and aftertaste | Not acceptable |

The same method can be used to prepare juices and juice drinks from other fruits, such as apples, lemons, apricots, cherries, pineapples, mangoes, etc.

Example 7

Low-Calorie Carbonated Beverage

A carbonated beverage according to formula presented below was prepared.

| | Quantity, % | | |
|---|---|---|---|
| Ingredients | Sample 1 | Sample 2 | Sample 3 |
| Sucrose | 5.5 | 5.5 | 5.5 |
| Cola flavor | 0.340 | 0.340 | 0.340 |
| ortho-Phosphoric acid | 0.100 | 0.100 | 0.100 |
| Sodium citrate | 0.310 | 0.310 | 0.310 |
| Sodium benzoate | 0.018 | 0.018 | 0.018 |
| Citric acid | 0.018 | 0.018 | 0.018 |
| Rebaudioside A | 0.003 | 0.003 | 0.003 |
| Glucosyl stevia composition | 0.05 | 0.06 | 0.05 |
| Carbonated water | to 100 | to 100 | to 100 |

The sensory properties were evaluated by 20 panelists. The results are summarized in Table 4.

TABLE 4

Evaluation of low-calorie carbonated beverage samples

| | Number of panelists detected the attribute | | |
|---|---|---|---|
| Taste attribute | Sample No. 1 | Sample No. 2 | Sample No. 3 |
| Bitter taste | 10 | 0 | 11 |
| Astringent taste | 12 | 0 | 10 |
| Aftertaste | 14 | 0 | 14 |
| | Comments | | |
| Quality of sweet taste | Bitter aftertaste (10 of 20) | Clean (20 of 20) | Bitter aftertaste (12 of 20) |
| Overall evaluation | Satisfactory (3 of 20) | Satisfactory (20 of 20) | Satisfactory (4 of 20) |

The above results show that the beverages prepared using Sample 2 possessed the best organoleptic characteristics.

Example 8

Diet Cookies

Flour (50.0%), margarine (30.0%) fructose (10.0%), maltitol (8.0%), whole milk (1.0%), salt (0.2%), baking powder (0.15%), vanillin (0.1%) and different glucosyl stevia compositions (0.03% for Samples 1 and 3, and 0.04% for Sample 2) were kneaded well in dough-mixing machine. The obtained dough was molded and baked in oven at 200° C. for 15 minutes. Glucosyl stevia compositions were represented by Samples 1, 2 and 3, obtained according to EXAMPLES 2, 3 and 5, respectively.

The sensory properties were evaluated by 20 panelists. The best results were obtained in samples prepared by high glucosyl stevia composition containing derivatives with up to 20 α-1,4-glucosyl residues (Sample 2). The panelists noted rounded and complete flavor profile and mouthfeel in cookies prepared with Sample 2.

Example 9

Yoghurt

Different glucosyl stevia compositions (0.03% for Samples 1 and 3, and 0.04% for Sample 2) and sucrose (4%) were dissolved in low fat milk. Glucosyl stevia compositions were represented by Samples 1, 2 and 3, obtained according to EXAMPLES 2, 3 and 5, respectively. After pasteurizing at 82° C. for 20 minutes, the milk was cooled to 37° C. A starter culture (3%) was added and the mixture was incubated at 37° C. for 6 hours then at 5° C. for 12 hours.

The sensory properties were evaluated by 20 panelists. The best results were obtained in samples prepared by high glucosyl stevia composition containing derivatives with up to 20 α-1,4-glucosyl residues (Sample 2). The panelists noted rounded and complete flavor profile and mouthfeel in samples prepared with Sample 2.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. A process for producing a glucosyl *stevia* composition, comprising the steps of:
   adding starch into water to form a starch suspension;
   adding a mixture of α-amylase and a first portion of CGTase into the starch suspension and incubating the starch suspension, resulting in a liquefied starch suspension;
   inactivating the α-amylase by low pH heat treatment;
   adding steviol glycosides into the liquefied starch suspension, resulting in a reaction mixture;
   adding a second portion of CGTase into the reaction mixture and incubating the reaction mixture as a first transglucosylation step;
   removing non-reactant maltooligosaccharides by contacting the reaction mixture with a macroporous adsorbent resin to obtain a mixture of α-1,4-glucosyl derivatives;
   subjecting the mixture of α-1,4-glucosyl derivatives to a second transglucosylation step by CGTase in the presence of starch as a glucose donor to produce the glucosyl *stevia* composition;
   wherein the glucosyl *stevia* composition comprises steviol glycosides and their derivatives having up to twenty α-1,4-glucosyl residues.

2. The process according to claim 1, wherein the mixture of α-amylase and CGTase contains about 0.001-0.2 KNU of α-amylase per one unit of CGTase.

3. The process of claim 1, wherein the mixture of α-amylase and CGTase contains about 0.05-0.1 KNU of α-amylase per one unit of CGTase.

4. The process according to claim 1, wherein the weight of added steviol glycosides is about equal to that of the starch used to make the liquefied starch suspension.

5. The process according to claim 1, wherein the added steviol glycosides are selected from the group consisting of stevioside, Rebaudioside A, Rebaudioside B, Rebaudioside C, Rebaudioside D, Rebaudioside E, Rebaudioside F, dulcoside A, steviolbioside, rubusoside, other steviol glycosides found in *Stevia rebaudiana* Bertoni plant, mixtures thereof, and glucosylated derivatives thereof.

6. The process according to claim 1, wherein the starch suspension with the added α-amylase and CGTase is incubated for a period of about 0.5 to 2 hours at about 75-80° C. to result in the liquefied starch suspension.

7. The process according to claim 1, wherein the reaction mixture of the first tranglucosylation step with the added CGTase is incubated for a period of 12 to 48 hours at about 55-75° C.

8. The process according to claim 1, wherein the CGTase used in each step is produced by cultures of *Bacillus stearothermophilus*.

9. The process according to claim 1, wherein the CGTase added in the first or second tranglucosylation step is added at amount of about 0.2-4 units per gram of solids.

10. The process according to claim 1, wherein the CGTase added in the first or second tranglucosylation step is added at amount of about 0.5-1.2 units per gram of solids.

11. The process according to claim 1, further comprising the step of decolorizing the glucosyl *stevia* composition.

12. The process according to claim 11, wherein the decolorizing is performed using activated carbon, ion exchange resins, or membranes, said membranes being selected from the group consisting of ultrafiltration, nanofiltration, and reverse osmosis membranes.

13. The process of claim 1, further comprising the step of removing maltooligosaccharides from the glucosyl *stevia* composition by contacting the glucosyl *stevia* composition with a macroporous adsorbent resin.

14. The process of claim 13, wherein removing maltooligosaccharides from the glucosyl *stevia* composition further comprises removing non-diterpene compounds.

15. The process according to claim 1, further comprising the step of desalting the glucosyl *stevia* composition, wherein the desalting is performed by passing the glucosyl *stevia* composition through columns packed with ion exchange resins or membranes, said membranes being selected from the group consisting of ultrafiltration, nanofiltration, and reverse osmosis membranes.

16. The process according to claim 1, wherein the glucosyl *stevia* composition has at least about 95% total steviol glycosides on an anhydrous basis.

17. The process according to claim 1, wherein the glucosyl *stevia* composition has less than 10% unreacted steviol glycosides on an anhydrous basis.

18. A sweetener composition comprising the glucosyl *stevia* composition made by the process of claim 1, and an additional sweetening agent selected from the group consisting of: *stevia* extract, steviol glycosides, stevioside, Rebaudioside A, Rebaudioside B, Rebaudioside C, Rebaudioside D, Rebaudioside E, Rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols, and a combination thereof.

19. A flavor composition comprising the glucosyl *stevia* composition made by the process of claim 1, and an additional flavoring agent selected from the group consisting of: lemon, orange, fruit, banana, grape, pear, pineapple, mango, bitter almond, cola, cinnamon, sugar, cotton candy, vanilla, and a combination thereof.

20. A food ingredient comprising the glucosyl *stevia* composition made by the process of claim 1, and an additional food ingredient selected from the group consisting of: acidulants, organic and amino acids, coloring agents, bulking agents, modified starches, gums, texturizers, preservatives, antioxidants, emulsifiers, stabilizers, thickeners, gelling agents, and a combination thereof.

21. A food, beverage, cosmetic or pharmaceutical product comprising the glucosyl *stevia* composition made by the process of claim 1.

22. The process of claim 1, further comprising the step of removing maltooligosaccharides compounds from the glucosyl *stevia* composition, wherein said removing is conducted with a plurality of sequentially connected columns packed with a macroporous adsorbent resin, followed by washing the columns with water, then washing with about 10-50% (v/v) ethanol, disconnecting the columns, and then eluting each column individually with 30-100% ethanol to result in an eluate containing the glucosyl *stevia* composition.

23. The process of claim 1, wherein removing maltooligosaccharides further comprises removing non-diterpene compounds.

* * * * *